(12) United States Patent
Rommel (10) Patent No.: US 11,599,564 B2
(45) Date of Patent: Mar. 7, 2023

(54) TRANSMISSION OF A DATA SET AND PROVISION OF DATA TRANSMISSION INFORMATION

(71) Applicant: Siemens Healthcare GmbH, Erlangen (DE)

(72) Inventor: Michael Rommel, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 17/287,687

(22) PCT Filed: Oct. 2, 2019

(86) PCT No.: PCT/EP2019/076700
§ 371 (c)(1),
(2) Date: Apr. 22, 2021

(87) PCT Pub. No.: WO2020/094302
PCT Pub. Date: May 14, 2020

(65) Prior Publication Data
US 2021/0312287 A1    Oct. 7, 2021

(30) Foreign Application Priority Data
Nov. 8, 2018  (DE) .................. 10 2018 219 070.4

(51) Int. Cl.
*G06F 15/173*    (2006.01)
*G06F 16/28*     (2019.01)
*H04L 67/12*     (2022.01)

(52) U.S. Cl.
CPC ............ *G06F 16/285* (2019.01); *H04L 67/12* (2013.01)

(58) Field of Classification Search
CPC ............................. G06F 16/285; H04L 67/12
See application file for complete search history.

(56) References Cited

U.S. PATENT DOCUMENTS

2003/0223755 A1* 12/2003 Tsai ............... H04B 10/1141
                                                    398/135
2009/0125555 A1   5/2009 Stanis et al.
(Continued)

FOREIGN PATENT DOCUMENTS

CN      105426517 A      3/2016
WO   WO 2018005966 A1   1/2018

OTHER PUBLICATIONS

TInternational Search Report PCT/ISA/210 for International Application No. PCT/EP2019/076700 dated Dec. 9, 2019.
(Continued)

*Primary Examiner* — Padma Mundur
(74) *Attorney, Agent, or Firm* — Harness, Dickey & Pierce, P.L.C.

(57) ABSTRACT

An embodiment relates to the transmission of a data set to a central data store. A data set is received via a data source. Furthermore, country information is optionally received via the data source. Furthermore, a data classification is determined based on the data set via the data source. Furthermore, the data classification and optionally the country information are sent to a server via the data source. Furthermore, data transmission information from the server is received via the data source. In this context, the data transmission information is based on the data classification and optionally on the country information and the data transmission information relates to the permissibility of the transmission of the data set. Furthermore, the data set is transmitted to the central data store in dependence on the data transmission information.

30 Claims, 5 Drawing Sheets

(56) References Cited

U.S. PATENT DOCUMENTS

| | | | |
|---|---|---|---|
| 2010/0042583 A1* | 2/2010 | Gervais | G06Q 40/08 |
| | | | 707/E17.014 |
| 2013/0269035 A1 | 10/2013 | Bajaj et al. | |
| 2013/0304742 A1 | 11/2013 | Roman et al. | |
| 2014/0188804 A1* | 7/2014 | Gokhale | G06F 11/1448 |
| | | | 707/645 |
| 2016/0173623 A1* | 6/2016 | Broussard | H04L 63/107 |
| | | | 713/168 |
| 2018/0024578 A1* | 1/2018 | Ahuja | G06F 1/206 |
| | | | 700/300 |
| 2018/0225357 A1* | 8/2018 | Greco | G06V 10/98 |
| 2021/0056529 A1 | 2/2021 | Schneider | |

OTHER PUBLICATIONS

"Modular programming", Wikipedia, Oct. 13, 2018 (Oct. 13, 2018), pp. 1-5, XP055647671.
Dferdaisy et al: "Picture archiving and communication system", Wikipedia, Sep. 2, 2018 (Sep. 2, 2018), pp. 1-9, XP055647650.
Zhu, Wei-Dong [et al.]: Content Manager implementation and migration cookbook. IBM, International Technical Support Organization, Apr. 2006.—ISBN 0-7384-9620-0.
German Office Action for German Application No. 10 2018 219 070.4 dated Nov. 21, 2019.
DGP for German Office Action 10 2018 219 070.4 dated Dec. 5, 2019.
Written Opinion PCT/ISA/237 for International Application No. PCT/EP2019/076700 dated Dec. 9, 2019.

* cited by examiner

| | | | |
|---|---|---|---|
| US | US | NPI | T |
| US | US | ANI | C |
| US | US | PI | F |
| DE | US | NPI | T |
| DE | US | ANI | F |
| DE | US | PI | F |

| | | |
|---|---|---|
| INSTA | 2018/01/01 | |
| INSTB | 2017/01/01 | 2017/12/31 |
| INSTC | 2017/01/01 | 2017/12/31 |
| INSTC | 2018/07/01 | |

TRANSMISSION OF A DATA SET AND PROVISION OF DATA TRANSMISSION INFORMATION

PRIORITY STATEMENT

This application is the national phase under 35 U.S.C. § 371 of PCT International Application No. PCT/EP2019/076700 which has an International filing date of Oct. 2, 2019, which designated the United States of America and which claims priority to German application number DE 102018219070.4 filed Nov. 8, 2018, the entire contents of each of which are hereby incorporated herein by reference.

FIELD

Embodiments described herein relate generally to transmission of a data set and provision of data transmission information.

BACKGROUND

Medical apparatuses, in particular imaging medical apparatuses such as computed tomography scanners, magnetic resonance scanners, X-ray apparatuses or ultrasound apparatuses are frequently connected via a data link to a control center or a central data store. This data link enables, for example, remote maintenance of the medical apparatus from the control center. In this context, the medical apparatus and the control center can be located in different countries.

In this context, the transmission of data via the data link is subject to a wide variety of restrictions. For example, legal regulations may only allow the transmission of certain types of data and/or transmission may only be allowed to certain countries. Furthermore, the permissibility of a transmission may depend upon whether there is a contractual arrangement between the operator of the medical apparatus and the operator of the control center.

Therefore, the medical apparatuses must be suitably configured so that transmission of data only takes place when transmission of the data is actually allowed. However, the configuration of the individual medical apparatuses is very complex, in particular when the configuration of a large number of medical apparatuses has to be adapted and in particular when they have to be frequently adapted to changing circumstances.

Alternatively, it is known to transmit data from the medical apparatus to the control center in all cases or unconditionally and only to decide in the control center whether the data transmission was allowed and to delete data transmitted without permission after checking in the control center.

SUMMARY

The inventors have discovered that transmission of the medical apparatus to the control center in all cases or unconditionally, in particular, has the disadvantage that the data link was unnecessarily burdened by the data transmission.

At least one embodiment provides a solution for data transmission that results in less configuration effort and/or a lower load on the data link.

Embodiments are directed to a method for the transmission of a data set, a method for the provision of data transmission information, a data source, a server, a computer program product and a computer-readable storage medium according to the independent claims. Advantageous developments are disclosed in the dependent claims and in the description.

The following describes the achievement of the embodiments according to the invention both with respect to the apparatuses and with respect to the method. Features, advantages or alternative embodiments mentioned in this context are likewise also to be transferred to the other claimed subject matter and vice versa. In other words, the substantive claims (which are, for example, directed at an apparatus) can also be developed with the features described or claimed in connection with a method. Herein, the corresponding functional features of the method are embodied by corresponding substantive modules.

Furthermore, the following describes the achievement of the embodiments according to the invention both with respect to a method for transferring a data set or a client and with respect to a method for the provision of data transmission information or a server. Features, advantages or alternative embodiments mentioned in this context are likewise also to be transferred to the other claimed subject matter and vice versa. In other words, the claims for the method for transferring the data set or the client can also be developed with features described or claimed in connection with the method for the provision of data transmission information or the server.

In a first embodiment, the invention relates to a method for the transmission of a data set to a central data store. The method is based on the fact that a data set is received via a data source. Herein, the reception of the data set in particular takes place via a first interface of the data source. The method is furthermore based on the fact that a data classification is determined based on the data set via the data source; in this context, the determination in particular takes place via a first computing unit of the data source. Furthermore, this data classification and the country information is sent to a server via the data source, in particular via a second interface of the data source. Furthermore, data transmission information is received from the server via the data source, wherein the reception in particular takes place via the second interface of the data source. In this context, the data transmission information is based on the country information and the data classification, and the data transmission information relates to the permissibility of the transmission of the data set. Furthermore, the data set is transmitted to the central data store in dependence on the data transmission information.

The invention relates in a second embodiment to a computer-implemented method for the provision of data transmission information comprising the reception of a data classification via a server, the determination of data transmission information via the server, wherein data transmission information is based on data classification, and the provision of the data transmission information for a data source via the server. In particular, the data classification relates to a data set.

In a third possible embodiment, the invention relates to a method for the transmission of a data set to a central data store comprising:

receiving the data set via a data source, determining a data classification based on the data set via the data source, transferring the data classification from the data source to a server, determining data transmission information via the server, wherein data transmission information is based on the data classification, wherein the data transmission information relates to the permissibility of the transmission of the data set, transmitting the data transmission information from the server to the data source, and transmitting the data set to the central data store in dependence on the data transmission information via the data source.

In a fourth embodiment, the invention relates to a data source for transmitting a data set to a central data store comprising:

a first interface embodied to receive the data set, furthermore embodied to send the country information and a data classification to a server, furthermore embodied to receive data transmission information from the server, wherein the data transmission information is based on the data classification, wherein the data transmission information relates to the permissibility of the transmission of the data set, furthermore embodied to transmit the data set to the central data store in dependence on the data transmission information, and a first computing unit embodied to determine the data classification based on the data set.

In a fifth embodiment, the invention relates to a server for providing data transmission information comprising:

a second interface embodied to receive a data classification, furthermore embodied to provide data transmission information for a data source, and a second computing unit embodied to determine the data transmission information, wherein the data transmission information is based on the data classification.

In a possible sixth embodiment, the invention relates to a data transmission system comprising a data source according to the fourth embodiment of the invention and comprising a server according to the fifth embodiment of the invention.

In a seventh embodiment, the invention relates to a computer program product with a computer program, which can be loaded directly into a first storage unit of a client, with program sections for carrying out all the steps of the method for the transmission of a data set according to an embodiment of the invention when the program sections are executed by the client, and/or which can be loaded directly into a second storage unit of a server, with program sections for carrying out all the steps of an embodiment of the method for providing data transmission information according to an embodiment of the invention when the program sections are executed by the server.

In a possible eighth embodiment, the invention relates to a computer program product with a computer program, which can be loaded directly into a first storage unit of a client, with program sections for carrying out all the steps of an embodiment of the method for the transmission of a data set according to an aspect of the invention when the program sections are executed by the client.

In a possible ninth embodiment, the invention relates to a computer program product with a computer program, which can be loaded directly into a second storage unit of a server, with program sections for carrying out all the steps of an embodiment of the method for providing data transmission information according to an embodiment of the invention when the program sections are executed by the server.

In a tenth embodiment, the invention relates to a computer-readable storage medium on which program sections which can be read and executed by a client are stored for carrying out all the steps of an embodiment of the method for the transmission of a data set according to an embodiment of the invention when the program sections are executed by the client, and/or on which program sections which can be read and executed by a server are stored for carrying out all the steps of the method for providing data transmission information according to an embodiment of the invention when the program sections are executed by the server.

In a possible eleventh embodiment, the invention relates to a computer-readable storage medium on which program sections which can be read and executed by a client are stored for carrying out all the steps of an embodiment of the method for the transmission of a data set according to an embodiment of the invention when the program sections are executed by the client.

In a possible twelfth embodiment, the invention relates to a computer-readable storage medium on which program sections which can be read and executed by a server are stored for carrying out all the steps of an embodiment of the method for providing data transmission information according to an embodiment of the invention when the program sections are executed by the server.

BRIEF DESCRIPTION OF THE DRAWINGS

The above-described properties, features and advantages of this invention and the manner in which these are achieved will become clearer and more plainly comprehensible in conjunction with the following description of the example embodiments explained in more detail in conjunction with the drawings. This description does not restrict the invention to these example embodiments. In the different figures, the same components are given identical reference characters. The figures are not generally to scale. The figures show.

Where not explicitly stated, but advisable and within the spirit of the invention, individual example embodiments, individual sub-aspects or features thereof can be combined or interchanged without departing from the scope of the present invention. Where applicable, advantages of the invention described with reference to one example embodiment also apply to other embodiments without being explicitly named.

DETAILED DESCRIPTION OF THE EXAMPLE EMBODIMENTS

In a first embodiment, the invention relates to a method for the transmission of a data set to a central data store. The method is based on the fact that a data set is received via a data source. Herein, the reception of the data set in particular takes place via a first interface of the data source. The method is furthermore based on the fact that a data classification is determined based on the data set via the data source; in this context, the determination in particular takes place via a first computing unit of the data source. Furthermore, this data classification and the country information is sent to a server via the data source, in particular via a second interface of the data source. Furthermore, data transmission information is received from the server via the data source, wherein the reception in particular takes place via the second interface of the data source. In this context, the data transmission information is based on the country information and the data classification, and the data transmission information relates to the permissibility of the transmission of the data set. Furthermore, the data set is transmitted to the central data store in dependence on the data transmission information.

A data set is a group of data fields with related content. In particular, a data set can be a file, a part of a file and/or an entry in a database. A data set can in particular be a medical data set. In this context, a medical data set comprises medical data relating to a patient (for example personal data, medical image data, laboratory reports, structured diagnoses and/or unstructured diagnoses) and/or data relating to a medical apparatus (for example log data).

A data classification relates to the type of a data set and/or the type of the content of a data set. In particular, the data classification can comprise the format of the data set (for example "PDF", "Text", "Dicom"). In particular, a data classification can comprise a value from a predetermined list of possible values (for example, a value from the list "public", "internal" and "confidential") that applies to the data set; furthermore a data classification can comprise one or more key-value pairs relating to the data set (for example with the key "medical data" and the value "True", or with the key "personal data" and the value "False"). In particular, the data classification can comprise whether the respective data set is a medical data set and/or personal data. Furthermore, the data classification can also comprise metadata of the data set, for example the file name of the data set or a product model of the medical apparatus that generated the data set.

Data transmission information relates to the permissibility of the transmission of a data set. In other words, it can be determined based on the data transmission information whether a data set can and/or may be transmitted. The permissibility can relate to technical permissibility (for example compatibility) and/or legal permissibility. Technical permissibility can in particular also relate to a limited data transmission rate between two countries (so that data sets are only transmitted when only a few other data sets are transmitted) or to a limited time period for the transmission of data sets (so that data sets in certain categories with low priority should only take place at predetermined times at which few data sets with high priority are transmitted, for example at night).

In particular, the data transmission information can comprise a binary data field, wherein transmission of the data set is permitted at a first value of the binary data field, and wherein the transmission of the data set is not permitted at a second value of the binary data field. In particular, the data transmission information can also comprise a data field relating to a number of central data stores, wherein the data field lists the central data stores permitted for the transmission. In this case, the number can also be zero when transmission of the data set is not permitted.

The inventor has recognized that the method described enables the data transmission information to be ascertained based on the data classification sent by the data source without the actual data set having to be transferred to the server. In particular, therefore, less data has to be transferred from the data source to the server, in particular when the transmission of the data set is not permitted.

Furthermore, the described method for ascertaining the permissibility of the transmission of the data set does not require the rules and/or data required to ascertain the data classification based on the data classification to be available to the data source. In particular, therefore, if this data and/or these rules are changed, the change does not have to be implemented in a plurality of data sources. The necessity of such an implementation in a plurality of data sources would, for example, lead to possibly erroneous transmissions of data sets in the event of an interrupted link or temporary failures of the data source.

According to a further embodiment of the invention, the data classification is sent by invoking an interface function of the server, and the data transmission information is the output value of the interface function. The interface function is advantageously a function of an application programming interface ("API") of the server.

The inventor has recognized that the use of an interface function enables the data source and the server to be operated as logically separate modules. In particular, therefore, the actual implementation of the interface function on the server can be changed without changes to the data source and/or the programming thereof being necessary. In particular, therefore, no logic needs to be stored and/or provided on the data source in order to ascertain data transmission information based on a data classification. Thus, when this logic is changed only the server needs to be adapted, and not the individual data sources. This leads to increased consistency of the system and a reduction in the erroneous transmission of data sets.

According to a further embodiment of the invention, the method furthermore comprises the reception of country information via the data source; furthermore when the data classification is sent the country information is also sent to the server via the data source; furthermore the data transmission information is based on the country information. In this context, the reception of the country information in particular takes place via the first interface of the data source. The country information can in particular be sent also by invoking the interface function of the server.

Country information relates to a source country and/or a target country of a data set to be transmitted. In this context, the source country is in particular the country in which the data source is located and the target country the country in which the central data store is located. A country (for example, a source country or a target country) can be a state, a group of states or a region within one or more states. In particular, a country can be characterized by uniform legislation with respect to the storage and/or transmission of data sets.

The inventor has recognized that the method described can be used to ascertain the data transmission information based on the country information sent by the data source without the actual data set having to be transferred to the server. In particular, therefore, less data has to be transferred from the data source to the server, in particular when the transmission of the data set is not permitted.

Furthermore, the described method for ascertaining the permissibility of the transmission of the data set does not require the rules and/or data required to ascertain the data classification based on the country information to be available to the data source. In particular, therefore, if this data and/or these rules are changed, the change does not have to be implemented in a plurality of data sources. The necessity of such an implementation in a plurality of data sources would, for example, lead to possibly erroneous transmission of data sets in the event of an interrupted link or temporary failures of the data source.

According to a further embodiment of the invention, the country information comprises source country information and target country information. The source country information in particular relates to the source country of the data set, and the target country information in particular relates to the target country of the data set. The inventor has recognized that the use of both types of information enables a particularly large number of unnecessary transmissions of data sets to be prevented. In particular, this enables situations to be addressed in which the transmission of a data set from a first source country to a target country is (technically and/or legally) permitted, but a transmission of the data set from a second source country to the target country is (technically and/or legally) impermissible. Likewise, situations can be addressed in which the transmission of a data set from a source country to a target country is (technically and/or legally) permitted, but a transmission of the data set from the source country to a second target country is (technically and/or legally) impermissible. In these situations, it is in particular possible for (technically and/or legally) impermissible transmissions of the data set to be prevented.

According to a further embodiment of the invention, the data transmission information comprises a status variable, wherein the transmission of the data set takes place when the status variable assumes a first value, and wherein the transmission of the data set does not take place when the status variable assumes a second value. In particular, the data transmission information can be identical to the status variable.

In other words, the method comprises the step of the transmission of the data set to the central data store via the data source when the status variable assumes the first value and the method comprises a step of stopping the data set via the data source when the status variable assumes the second value.

The inventor has recognized that data transmission information comprising such a status variable enables the permissibility of the transmission of the data set to be uniquely established. In particular, therefore, no further steps of the data source are necessary to ascertain permissibility based on the data transmission information. This enables the method to be performed very efficiently on the part of the data source.

According to a further embodiment of the invention, the data classification is contained in metadata of the data set. In this context, metadata is structured information about the content of other data. In this context, metadata can be contained in the data set or be stored independently of the data set. The inventor has recognized that the fact that the data classification is contained in the metadata of the data set makes the data classification less prone to errors.

According to a further embodiment of the invention, the determination of the data classification comprises the application of a regular expression and/or a trained function, in particular a trained neural network, to the data set.

In this context, the application of a regular expression in particular comprises the comparison of the data set with the regular expression (a technical term is "pattern matching"); in particular it can be determined whether the regular expression can be found in the file name or file path name.

In particular, in this context, the trained function is based on training data sets and assigned training data classifications. In particular, a training data classification is assigned to each of the training data sets. In this context, the training of the trained function can in particular be based on a comparison of the training data classification with the output value of the trained function, wherein the output value is the result of the application of the trained function to the assigned training data set. In this context, the training can in particular be based on backpropagation. In other words, the trained function can be trained via a machine learning algorithm.

The inventor has recognized that the use of a trained function and/or a regular expression enables the data classification to be determined particularly efficiently. In particular, manual classification of the data set is not necessary.

The invention relates in a second embodiment to a computer-implemented method for the provision of data transmission information comprising the reception of a data classification via a server, the determination of data transmission information via the server, wherein data transmission information is based on data classification, and the provision of the data transmission information for a data source via the server. In particular, the data classification relates to a data set.

The inventor has recognized that a determination of the data transmission information based on the data classification is particularly efficient. In particular, no further details of the data set or the actual data set need to be known in order to ascertain the permissibility of a transmission of the data set. Furthermore, the logic for determining the data transmission information can be held centrally on the server and thus does not have to be distributed to individual data sources.

According to a further embodiment of the invention, on the reception of the data classification furthermore country information is received and the data transmission information is furthermore based on the country information.

The inventor has recognized that the data transmission information can be determined particularly efficiently based on the country information. In particular, based on the country information, certain data transmissions may be permitted or not permitted on a blanket basis.

According to a further embodiment of the invention, the data classification is received from a data source and the method comprises the determination of country information based on the data source. In particular, the country information can be determined based on the geographical location of the data source, in particular based on an IP address ("Internet protocol" address), based on a database of possible data sources and/or based on a serial number of the data source.

The inventor has recognized that the determination of country information means the country information does not have to be received. As a result, on the one hand, less data has to be transmitted and, on the other, this increases the security of the system since it is difficult to use incorrect or manipulated country information.

According to a further embodiment of the invention, the method for the provision of data transmission information furthermore comprises the determination of a first classifier, wherein the first classifier is stored in a first data table in relation to the country information and/or the data classification, and wherein the determination of the data transmission information is based on the first classifier. In this context, the first data table is in particular stored in a first storage unit of the server.

The inventor has recognized that, based on a first classifier stored in a first data table, it can be established particularly efficiently whether a data set can and/or may be transmitted. In particular, changes to the permissibility of the transmission of certain data sets can be implemented very efficiently by changing corresponding entries in the first data table.

According to a further embodiment of the invention, the method for the provision of data transmission information furthermore comprises the determination of a second classifier, wherein the second classifier is stored in a second data table in relation to contract information, and wherein the determination of the data transmission information is furthermore based on the second classifier.

In this context, the first data table can be identical to the second data table or alternatively the first data table and the second data table can also be different. Contract information indicates in particular whether there is a contractual arrangement between the operator of a data source and the operator of the server and/or whether there is a contractual arrangement between the operator of the data source and the operator of the central data store. The contract information can in particular indicate whether there is a contractual basis for the transmission and/or storage of the data set in the central data store.

The inventor has recognized that, based on a second classifier stored in a second data table, it can be established particularly efficiently whether a data set can and/or may be transmitted. In particular, changes to the permissibility of the transmission of certain data sets can be implemented very efficiently by changing corresponding entries in the second data table.

According to a further embodiment of the invention, in the method for the provision of a data transmission function, the determination of the second classifier only takes place when the first classifier has a predetermined value.

The inventor has recognized that only determining the second classifier in certain cases enables the number of queries to the second data table to be reduced. In particular, therefore, it is, for example, not necessary for the second classifier to be determined if the first classifier already states that transmission of the data set is not permitted.

According to a further possible embodiment of the invention, in the method for the provision of a data transmission function, the determination of the first classifier only takes place when the second classifier has a predetermined value.

The inventor has recognized that only determining the first classifier in certain cases enables the number of queries to the first data table to be reduced. In particular, therefore, it is, for example, not necessary for the first classifier to be determined if the second classifier already states that transmission of the data set is not permitted.

According to a further embodiment of the invention, the method for the provision of data transmission information comprises the determination of a modified data classification by applying a regular expression and/or a trained function to the data classification via the server. In particular, when the data classification comprises metadata of the data set, the modified data classification can relate to the content of the data set. In this context, the determination of the modified data classification can in particular take place via the computing unit of the server.

In particular, the data transmission information can be determined based not on the data classification but on the modified data classification. In particular, the first classifier can also be stored in a data table in relation to the modified data classification instead of in relation to the data classification.

The inventor has recognized that, by determining a modified data classification, it is possible to dispense with the fact that the actual data set comprises the data classification and also to dispense with the fact that the data source carries out the determination of the data classification. In particular, this enables the determination of the data classification to be carried out and maintained at a central point.

According to a further embodiment of the invention, in the method for the transmission of a data set to a central data store, the data transmission information is determined via a method for the determination of data transmission information according to the invention and the aspects thereof. The inventor has recognized that a combination of the two methods in particular enables the respective advantages of the methods to be combined.

In a third possible embodiment, the invention relates to a method for the transmission of a data set to a central data store comprising:

receiving the data set via a data source, determining a data classification based on the data set via the data source, transferring the data classification from the data source to a server, determining data transmission information via the server, wherein data transmission information is based on the data classification, wherein the data transmission information relates to the permissibility of the transmission of the data set, transmitting the data transmission information from the server to the data source, and transmitting the data set to the central data store in dependence on the data transmission information via the data source.

The method according to the third possible embodiment of the invention can in particular comprise the advantageous embodiments and developments of one of the methods for the transmission of a data set to a central data store and for providing data transmission information.

In a fourth embodiment, the invention relates to a data source for transmitting a data set to a central data store comprising:

a first interface embodied to receive the data set, furthermore embodied to send the country information and a data classification to a server, furthermore embodied to receive data transmission information from the server, wherein the data transmission information is based on the data classification, wherein the data transmission information relates to the permissibility of the transmission of the data set, furthermore embodied to transmit the data set to the central data store in dependence on the data transmission information, and a first computing unit embodied to determine the data classification based on the data set.

In a fifth embodiment, the invention relates to a server for providing data transmission information comprising:

a second interface embodied to receive a data classification, furthermore embodied to provide data transmission information for a data source, and a second computing unit embodied to determine the data transmission information, wherein the data transmission information is based on the data classification.

Such a data source and such a server can in particular be embodied to carry out the above-described methods according to the invention and the aspects thereof. The data source and the server are embodied to carry out these methods and the aspects thereof in that the first interface and the first computing unit or the second interface and the second computing unit are embodied to carry out the corresponding method steps.

In a possible sixth embodiment, the invention relates to a data transmission system comprising a data source according to the fourth embodiment of the invention and comprising a server according to the fifth embodiment of the invention.

In a seventh embodiment, the invention relates to a computer program product with a computer program, which can be loaded directly into a first storage unit of a client, with program sections for carrying out all the steps of the method for the transmission of a data set according to an embodiment of the invention when the program sections are executed by the client, and/or which can be loaded directly into a second storage unit of a server, with program sections for carrying out all the steps of an embodiment of the method for providing data transmission information according to an embodiment of the invention when the program sections are executed by the server.

In a possible eighth embodiment, the invention relates to a computer program product with a computer program, which can be loaded directly into a first storage unit of a client, with program sections for carrying out all the steps of an embodiment of the method for the transmission of a data set according to an aspect of the invention when the program sections are executed by the client.

In a possible ninth embodiment, the invention relates to a computer program product with a computer program, which can be loaded directly into a second storage unit of a server, with program sections for carrying out all the steps of an embodiment of the method for providing data transmission information according to an embodiment of the invention when the program sections are executed by the server.

In a tenth embodiment, the invention relates to a computer-readable storage medium on which program sections which can be read and executed by a client are stored for carrying out all the steps of an embodiment of the method for the transmission of a data set according to an embodiment of the invention when the program sections are executed by the client, and/or on which program sections which can be read and executed by a server are stored for carrying out all the steps of the method for providing data transmission information according to an embodiment of the invention when the program sections are executed by the server.

In a possible eleventh embodiment, the invention relates to a computer-readable storage medium on which program sections which can be read and executed by a client are stored for carrying out all the steps of an embodiment of the method for the transmission of a data set according to an embodiment of the invention when the program sections are executed by the client.

In a possible twelfth embodiment, the invention relates to a computer-readable storage medium on which program sections which can be read and executed by a server are stored for carrying out all the steps of an embodiment of the method for providing data transmission information according to an embodiment of the invention when the program sections are executed by the server.

A substantially software-based implementation has the advantage that it is also possible to retrofit servers and clients used to date in a simple way via a software update in order to work in the manner according to the invention. In addition to the computer program, such a computer program product can optionally comprise additional parts such as, for example, documentation and/or additional components and also hardware components, such as, for example, hardware keys (dongles etc.) for using the software.

Figure 1:
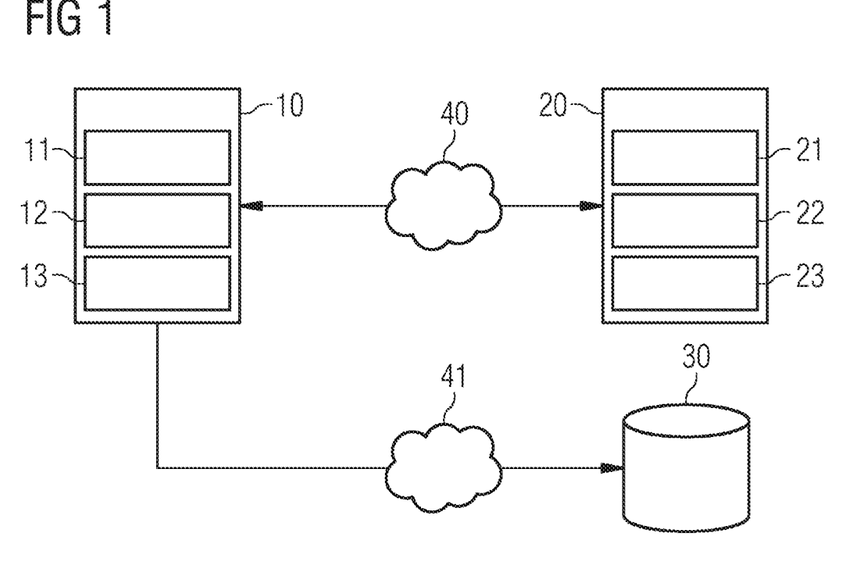
FIG. 1 shows units participating in the transmission of a data set.

FIG. 1 shows units participating in the transmission of the data set 50. A data source 10 is connected to a server 20 via a first network 40, furthermore the data source 10 is connected to a central data store 30 via a second network 41. In this context, the data set 50 is to be transmitted from the data source 10 to the central data store 30, wherein the technical and/or the legal permissibility for the transmission of the data set 50 from the server 20 is determined. The data source 10 shown here and the server 20 shown here are embodied (alone and/or in cooperation) to carry out a method according to the invention. The data source 10 is in particular spatially separate from the server 20, and the data source 10 is in particular spatially separate from the central data store 30.

In the example embodiment depicted, the data source 10 comprises a first interface 11, a first computing unit 12 and a first storage unit 13. Furthermore, the server 20 comprises a second interface 21, a second computing unit 22 and a second storage unit 23.

The data source 10 and/or the server 20 can in particular be a computer, a microcontroller or an integrated circuit. Alternatively, the data source 10 and/or the server 20 can be a real or virtual group of computers (a technical term for a real group is "cluster", a technical term for a virtual group is "cloud"). The data source 10 and/or the server 20 can also be embodied as a virtual system that is executed on a real computer or a real or virtual group of computers (a technical term is "virtualization").

A first and a second interface 11, 21 can be hardware or software interfaces (for example PCI bus, USB, Firewire, Ethernet, WLAN, in particular also interfaces that implement a mobile radio standard such as GPRS, EDGE, UMTS, LTE, 4G or 5G). The first and the second interface 11, 21 can comprise a plurality of separate sub-interfaces. A first and a second computing unit 12, 22 can have hardware elements or software elements, for example a microprocessor or a so-called FPGA ("field programmable gate array"). The first and the second computing unit 12, 22 can comprise a plurality of sub-computing units. A first and a second storage unit 13, 23 can be implemented as a non-permanent main memory (random access memory, RAM for short) or as a permanent mass storage device (hard disk drive, USB stick, SD card, solid state disk). The first and the second storage unit 13, 23 can comprise a plurality of sub-storage units.

In this context, the first network 40 and the second network 41 can be different networks, the first network 40 and the second network 41 can also be identical. In particular, the server 20 can comprise the central data store 30 or the central data store 30 can comprise the server 20.

The first and second network 40, 41 can be a local network (a technical term is "local area network", "LAN" for short) or a large-scale network (a technical term is "wide area network", "WAN" for short). An example of a local network is an intranet, an example of a large-scale network is the Internet. The first and the second network 40, 41 can in particular also be embodied as wireless, in particular as a WLAN ("wireless LAN", the term "WiFi" is also commonly used) or as a Bluetooth connection. The first and the second network 40, 41 can also be embodied as a combination of the examples given.

The central data store 30 can in particular be embodied as a dedicated database server, but it can also be embodied as a database application or applications which is or are operated on a server 20. In this context, the central data store 30 can in particular be embodied as a relational database, which can, for example, be queried via SQL ("structured query language"). However, the central data store 30 can also be embodied as a non-relational database.

Figure 2:
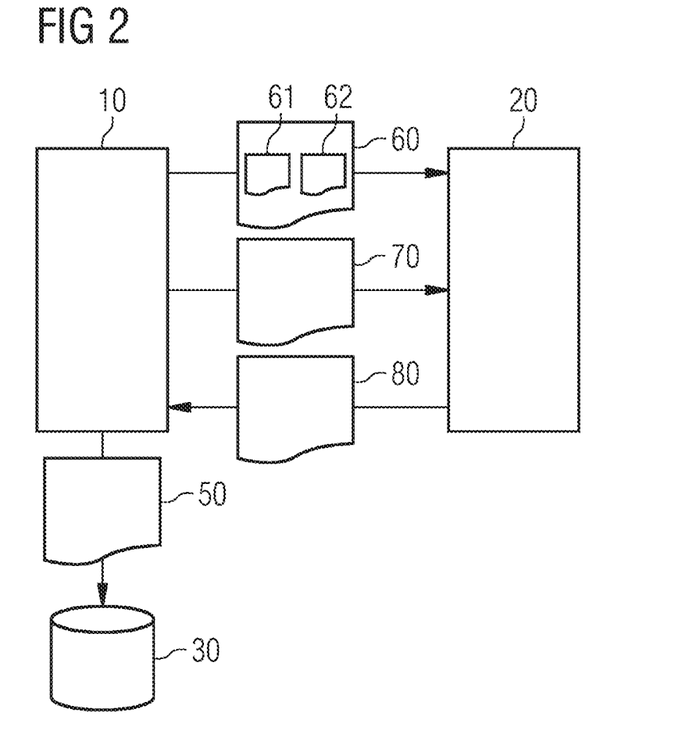
FIG. 2 shows a data flow diagram for the transmission of a data set.

FIG. 2 shows a data flow diagram for the transmission of the data set 50 from the data source 10 to the central data store 30. In this context, the data source 10 transfers country information 60 (comprising source country information 61 and target country information 62) and a data classification 70 to the server 20. In response, the server 20 transfers data transmission information 80 to the data source 10. In dependence on the data transmission information 80, the data source 10 transmits the data set 50 to the central data store 30.

Figure 3:
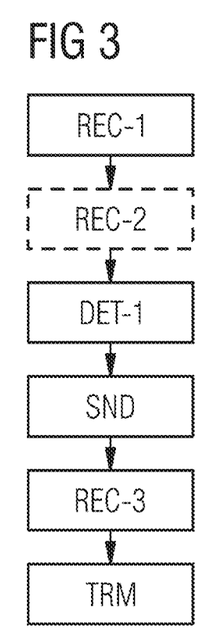
FIG. 3 shows a first example embodiment of the method for the transmission of a data set.

FIG. 3 is a flowchart of a first example embodiment of a method for the transmission of a data set 50.

The first step of the example embodiment depicted is the reception REC-1 of the data set 50 via a data source 10. In this example embodiment, the data set 50 is received via a first interface 11 of the data source 10.

In this example embodiment, the data set 50 is a log file of a medical technical installation. The log file can in particular comprise error messages from the medical technical installation and/or regular status reports from the medical technical installation. Alternatively, the data set 50 can also be a result data set, in particular an image data set, of the medical technical installation. A medical technical installation can in particular be an imaging medical technical installation (for example a computed tomography scanner, an X-ray installation or a magnetic resonance scanner) or a laboratory diagnostic installation. Alternatively, the data set 50 can also relate to another technical installation or be generated by another technical installation.

In this example embodiment, the technical installation or the medical technical installation comprises the data source 10 and the reception REC-1 of the data set 50 comprises retrieving the data set 50 from a memory of the medical technical installation and/or from a first storage unit 13 of the data source 10. Alternatively, the data source 10 can also be embodied as separate from the medical technical installation, for example, the data source 10 can be identical to a server in the hospital. In this case, in particular the technical or medical technical installation can transfer the data set 50 to the data source 10 or the data source 10 can receive the data set 50.

The second step of the example embodiment depicted is the reception REC-2 of country information 60 via the data source 10. The step of receiving REC-2 the country information 60 is an optional step. In this example embodiment, the country information 60 is received via the first interface 11 of the data source 10.

In this example embodiment, the country information 60 comprises source country information 61 and target country information 62. In this context, the source country information 61 corresponds to the country or jurisdiction in which the data source 10 is located. In this context, the target country information 62 corresponds to the country or jurisdiction in which the central data store 30 is located. In particular, when the server 20 comprises the central data store 30 or when the central data store 30 comprises the server 20, the country information 60 can also only comprise the source country information 61.

In the example embodiment depicted, the source country information 61 is stored in the first storage unit 13 of the data source 10 and the reception REC-2 of the country information 60 comprises the retrieval of the source country information 61 from the first storage unit 13 of the data source 10.

Alternatively, the source country information 61 can also be received together with the data set 50.

Alternatively, the source country information 61 can also be determined by the server 20, in particular based on an identifier of the data source 10 (for example an IP address or a serial number). In this case in particular, the reception of the source country information 61 can be dispensed with.

Furthermore, in the example embodiment depicted, the target country information 62 is determined based on the central data store 30. In particular when receiving REC-2 the country information 60, an address of the central data store 30, can be received, in particular in the form of a URL ("uniform resource locator") and the target country information 62 determined based on the URL or based on an IP address ("Internet protocol" address) ascertained via a DNS server ("domain name system" server).

Alternatively, the target country information 62 can also be determined by the server 20, in particular, the target country information 62 can be permanently stored in the server 20 or the target country information 62 is stored in the server in relation to the central data store 30.

The next step of the example embodiment depicted is the determination DET-1 of a data classification 70 based on the data set 50 via the data source 10. In this example embodiment, the data classification 70 is determined via a first computing unit 12 of the data source 10.

In this example embodiment, the data classification 70 can assume three different values, namely "non-personal", "anonymized" and "personal". In particular, the data classification 70 is "non-personal" when the data set 50 does not comprise any personal data (for example in the case of a machine's log data). In particular, the data classification 70 is "anonymized" when, although the data set 50 comprises data on a person, this data cannot be assigned to the person (for example image data for a patient without any details identifying the patient). In particular, the data classification 70 is "personal" when the data set 50 comprises data on a person that renders the data set 50 assignable to this person (for example a person's name or a person's unique identification number).

In this example embodiment, the data set 50 comprises the data classification 70 as metadata. Alternatively, the data classification 70 can also be determined via a trained function (for example a trained neural network) based on the data set 50, wherein the trained function has been trained based on training data sets and assigned training data classifications, for example using "backpropagation".

The next step of the example embodiment depicted is the sending SND-1 of the country information 60 and the data classification 70 to a server 20 via the data source 10. In this example embodiment, the country information 60 and the data classification 70 are sent via the first interface 11 of the data source 10.

In the example embodiment depicted, the sending SND-1 of the country information 60 and the data classification 70 takes place at the same time. However, the sending SND-1 of the country information 60 and the data classification 70 can also take place independently of one another.

Furthermore, in the example embodiment depicted, the sending SND-1 of the country information 60 and the data classification 70 takes place by invoking an interface function of the server 20, wherein the interface function of the server 20, the country information 60 and the data classification 70 are passed to the interface function as parameters. The interface function is in particular a function of an API. The API is in particular a RESTful API.

The next step of the example embodiment depicted is the reception REC-3 of data transmission information 80 from the server 20 via the data source 10. In this example embodiment, the reception REC-3 of the data classification 70 is performed via the first interface 11 of the data source 10.

In this example embodiment, the data transmission information 80 is the return value of the interface function of the server 20 which was invoked on the sending SND-1 of the country information 60 and the data classification 70.

Furthermore, the data transmission information 80 is based on the country information 60 and the data classification 70, wherein the data transmission information 80 relates to the permissibility of the transmission of the data set 50. In particular, in this example embodiment, the data transmission information 80 is a binary variable, wherein the value "0", "False" or a corresponding value is assumed when the transmission TRM of the data set 50 is not permitted, and wherein the value "1", "True" or a corresponding value is assumed when the transmission TRM of the data set 50 is permitted.

Alternatively, the data transmission information 80 can also comprise an address of the central data store 30, in particular a URL of the central data store 30. In this case, the data transmission information 80 can be empty or comprise an invalid address if the transmission TRM of the data set 50 is not permitted.

The last step of the example embodiment depicted is the transmission TRM of the data set 50 to the central data store 30 in dependence on the data transmission information 80 via the data source 10. In this example embodiment, the data set 50 is transmitted via the first interface 11 of the data source 10.

In this example embodiment, the transmission TRM takes place via FTP ("file transfer protocol"). Alternatively, it is also possible for other protocols to be used, for example via HTTP ("hypertext transfer protocol"). In particular, it is also possible for the transmission TRM to be performed via an encrypted protocol, for example based on SCP ("secure copy"), on FTPS ("file transfer protocol over secure sockets layer"), on SFTP ("secure shell file transfer protocol") or on HTTPS ("hypertext transfer protocol secure").

Figure 4:
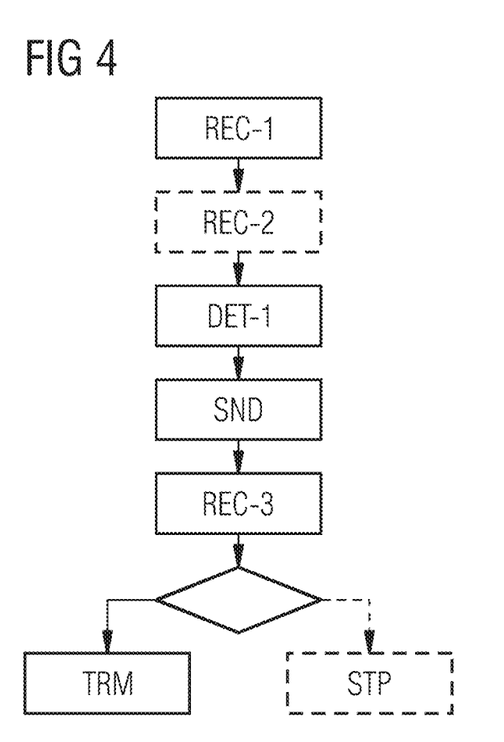
FIG. 4 shows a second example embodiment of the method for the transmission of a data set.

FIG. 4 is a flowchart of a second example embodiment of a method for the transmission of a data set 50.

The steps of the reception REC-1 of the data set 50, the reception REC-2 of country information 60, the determination DET-1 of a data classification 70, the sending SND-1 of the country information 60 and the data classification 70 and the reception REC-3 of data transmission information 80 can have all the advantageous embodiments and developments of the corresponding steps of the first example embodiment of the method for the transmission of the data set 50.

In the second example embodiment depicted, depending on the value of the data transmission information 80, either the data set 50 is transmitted TRM from the data source 10 to the central data store 30, or the data set 50 is stopped STP. In particular, the data set 50 is transmitted TRM when the data transmission information 80 has the value "1" or "True" and the data set 50 is stopped STP when the data transmission information 80 has the value "0" or "False".

If the data transmission information 80 comprises an address of the central data store 30, the data set 50 is in particular transmitted TRM when the data transmission information 80 comprises a valid address of the central data store 30 and the data set 50 is in particular stopped STP when the data transmission information 80 is empty.

Figure 5:
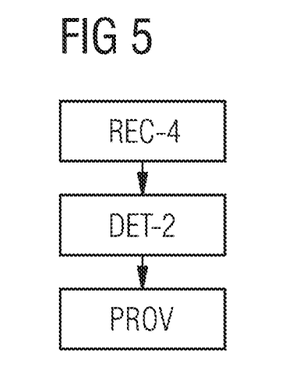
FIG. 5 shows a first example embodiment of the method for providing data transmission information.

FIG. 5 shows a flowchart of a first example embodiment of the method for the provision PROV of data transmission information 80.

The first step of the example embodiment depicted is the reception REC-4 of country information 60 and a data classification 70 via a server 20. In particular, the reception REC-4 takes place via a second interface 21 of the server 20. Alternatively, it is also possible for only a data classification 70 to be received.

In this example embodiment, the country information 60 comprises source country information 61 and target country information 62. Alternatively, the country information 60 can also comprise only the source country information 61 or only the target country information 62. In this context, the source country information 61 in particular relates to the country or the jurisdiction of a data source 10, and the target country information 62 relates to the country or the jurisdiction of the central data store 30 and/or the server 20.

In this context, the reception REC-4 in particular takes place in that an interface function of the server 20 is invoked and the country information 60 and the data classification 70 are handed over to the interface function as function parameters.

The following step of the example embodiment depicted is the determination DET-2 of data transmission information 80 via the server 20, wherein the data transmission information 80 is based on the country information 60 and the data classification 70. Here, the determination DET-2 in particular takes place via a second computing unit 22 of the server 20.

In this example embodiment, triples of country information 60, data classifications 70 and assigned data transmission information 80 are stored in a configuration file on the server 20. In this context, the configuration file is in particular stored within a second storage unit 23 of the server 20. This enables data transmission information 80 associated with country information 60 or data classification 70 to be changed centrally by adapting the respective entry in the configuration file. The configuration file can in particular be a database, in particular a relational database. This database can in particular comprise one or more data tables 85, 86.

Furthermore, the determination DET-2 of the data transmission information 80 can in particular be based on an available data transmission rate. The available data transmission rate can, for example, be a fixed value (for example the maximum data transmission rate between the data source 10 and the central storage unit); alternatively, it is also possible for the data transmissions performed or data transmissions scheduled at a point in time to be taken into account (outgoing from the data source 10 and/or incoming to the central data store 30). In particular, the data transmission information 80 can comprise a point in time from which the data transmission can be performed; in particular this point in time can be after the performance of the last ongoing and/or scheduled data transmission. This enables the data link between the data source and the central data store 30 to be utilized in a more distributed manner.

The following step of the example embodiment depicted is the provision PROV of the data transmission information 80 for a data source 10 via the server 20. The provision PROV in particular takes place via the second interface 21 of the server 20. In this context, the provision in particular takes place in that the data transmission information 80 is returned as a return value of the interface function invoked on reception REC-4.

Figure 6:
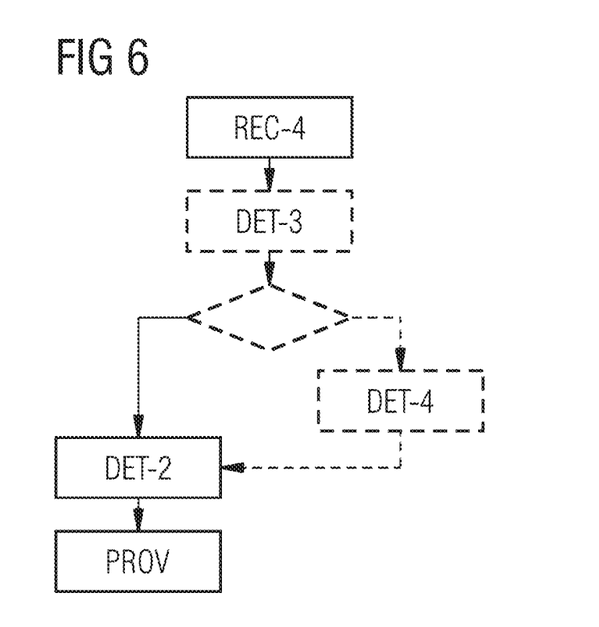
FIG. 6 shows a second example embodiment of the method for providing data transmission information.

FIG. 6 shows a flowchart of a second example embodiment of the method for the provision PROV of data transmission information 80. The second example embodiment comprises the steps of the reception REC-4 of country information 60 and a data classification 70 via a server 20 and the provision PROV of the data transmission information 80 for a data source 10 via the server 20; these steps can have all the advantageous embodiments and developments that were described in relation to the first example embodiment of the method for the provision PROV of data transmission information 80 or FIG. 5.

The example embodiment depicted furthermore optionally comprises the determination DET-3 of a first classifier 81, wherein the first classifier 81 is stored in a first data table 85 in relation to the country information 60 and/or the data classification 70.

In this example embodiment, the first classifier 81 can assume three different values. If the first classifier 81 assumes the value "T", data transmission is permitted in all cases. If the first classifier 81 assumes the value "F", data transmission is impermissible in all cases. If the first classifier 81 assumes the value "C", data transmission is only permitted when there is a contractual arrangement between an operator of the data source 10 and an operator of the central data store 30. The example embodiment depicted furthermore optionally comprises the determination DET-4 of a second classifier 82, 83, wherein the second classifier 82, 83 is stored in a second data table 86 in relation to contract information. In this example embodiment, the determination DET-4 of the second classifier 82, 83 only takes place when the first classifier has a predetermined value (here "C").

In this example embodiment, the second classifier 82, 83 comprises a first time stamp 82 and a second time stamp 83, wherein neither the first time stamp 82 nor the second time stamp 83 must have a value. In this context, the first time stamp 82 corresponds to the start of a contractual arrangement between an operator of the data source 10 and an operator of the central data store 30 and the second time stamp 83 corresponds to the end of a contractual arrangement between an operator of the data source 10 and an operator of the central data store 30. Alternatively, it is also possible for a binary value to be selected as the second classifier 82, 83, wherein the second classifier 82, 83 assumes a first value if there is a contractual arrangement between an operator of the data source 10 and an operator of the central data store 30 at the current point in time, and wherein the second classifier assumes a second value if there is no contractual arrangement between an operator of the data source 10 and an operator of the central data store 30 at the current point in time.

In this example embodiment, the determination DET-2 of the data transmission information 80 is based on the first classifier 81; furthermore the determination DET-2 of the data transmission information 80 is based on the second classifier 82, 83 when the determination DET-4 of the second classifier 82, 83 has taken place.

In particular, the value "0" or "False" is used as data transmission information 80 when the first classifier 81 has the value "F". Furthermore, the value "1" or "True" is used as data transmission information 80 when the first classifier 81 has the value "T".

If the first classifier 81 has the value "C", the data transmission information 80 assumes the value "1" or "True" when the first time stamp 82 is before the current time and the second time stamp 83 is after the current time, i.e. a contractual arrangement exists, in other cases, the data transmission information 80 assumes the value "0" or "False".

As an alternative to the value "0", the data transmission information 80 can also be empty and as an alternative to the value "1" the data transmission information 80 can also comprise a valid address, in particular a URL of the central data store 30.

Alternatively, in this example embodiment, the data classification 70 can comprise metadata of the data set 50, for example the file name of the data set 50 and a type and/or a serial number of the medical apparatus that generated the data set 50. In this context, the first classifier 81 can be stored in relation to this metadata; alternatively, it is possible (for example by applying a regular expression or a trained function) to determine a modified data classification, which is determined in relation to the first classifier 81. For example, it may be determined from a file name with the file extension "*.log" of a specific type of medical apparatuses that the associated data set 50 does not comprise any personal data.

Figure 7:
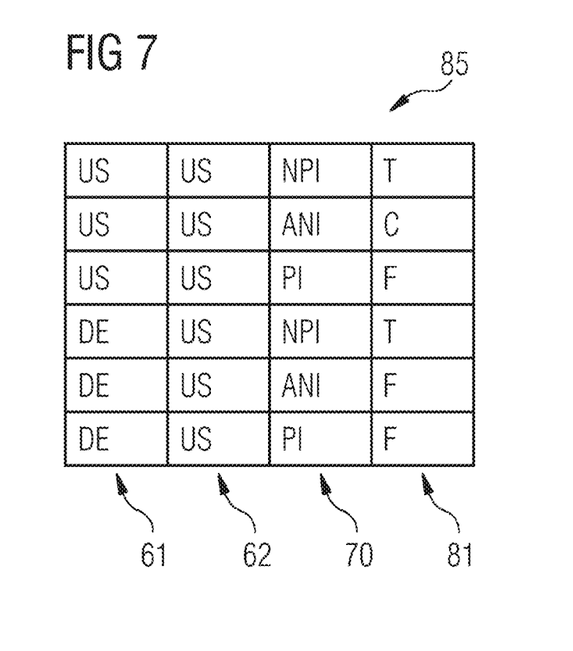
FIG. 7 shows a first data table.

FIG. 7 shows an example embodiment of a first data table 85. The first data table 85 comprises a plurality of rows, each row comprises source country information 61, target country information 62, a data classification 70 and a first classifier 81.

For example, the source country information 61 and the target country information 62 in the first row corresponds to "US" (for "United States of America"), the data classification 70 corresponds to "NPI" (for "non-personal"). The assigned first classifier is "T". Thus, this first row means that non-personal data can always be transmitted within the United States.

For example, the source country information 61 and the target country information 62 in the second row corresponds to "US"; the data classification 70 corresponds to "ANI" (for "anonymized"). The assigned first classifier is "C". Thus, this second row means that anonymized data can always be transmitted within the United States when there is a contractual relationship between the operator of the data source 10 and the operator of the central data store 30.

For example, the source country information 61 in the sixth row corresponds to "DE" (for "Germany") and the target country information 62 corresponds to "US", the data classification 70 corresponds to "PI" (for "personal"). The assigned first classifier is "F". Thus, this sixth row means that personal data can never be transmitted from Germany to the United States.

Figure 8:
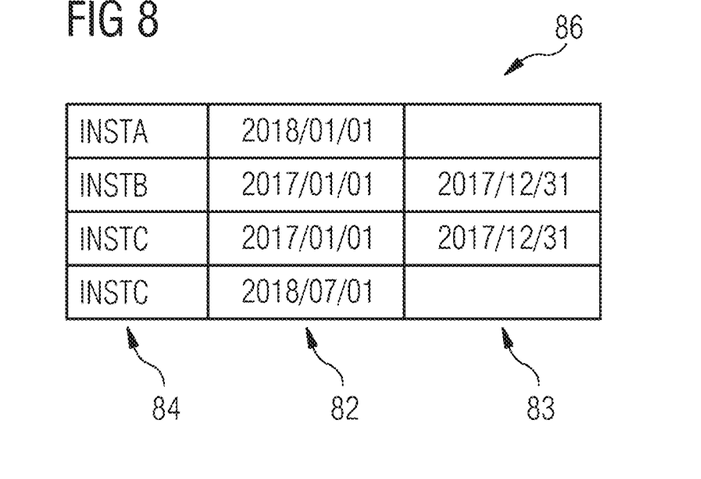
FIG. 8 shows a second data table.

FIG. 8 shows an example embodiment of a second data table 86. The second data table 86 comprises a plurality of rows, each row comprises an identifier 84 of an operator of a data source 10, a first time stamp 82 and a second time stamp 83.

In this context, the first row of the second data table 86 documents the fact that, for an operator with the identifier "INSTA", there is a contractual arrangement (with the operator of the server 20 and/or the central data store 30) from Jan. 1, 2018 which has been concluded for an indefinite time. The second row of the second data table 86 documents the fact that, for an operator with the identifier "INSTB", there was a contractual arrangement (with the operator of the server 20 and/or the central data store 30) between Jan. 1, 2017 and Dec. 31, 2017. The third and fourth row of the second data table 86 document the fact that, for an operator with the identifier "INSTC", there was or is a contractual arrangement (with the operator of the server 20 and/or the central data store 30) between Jan. 1, 2017 and Dec. 31, 2017 and from Jul. 1, 2018.

Figure 9:
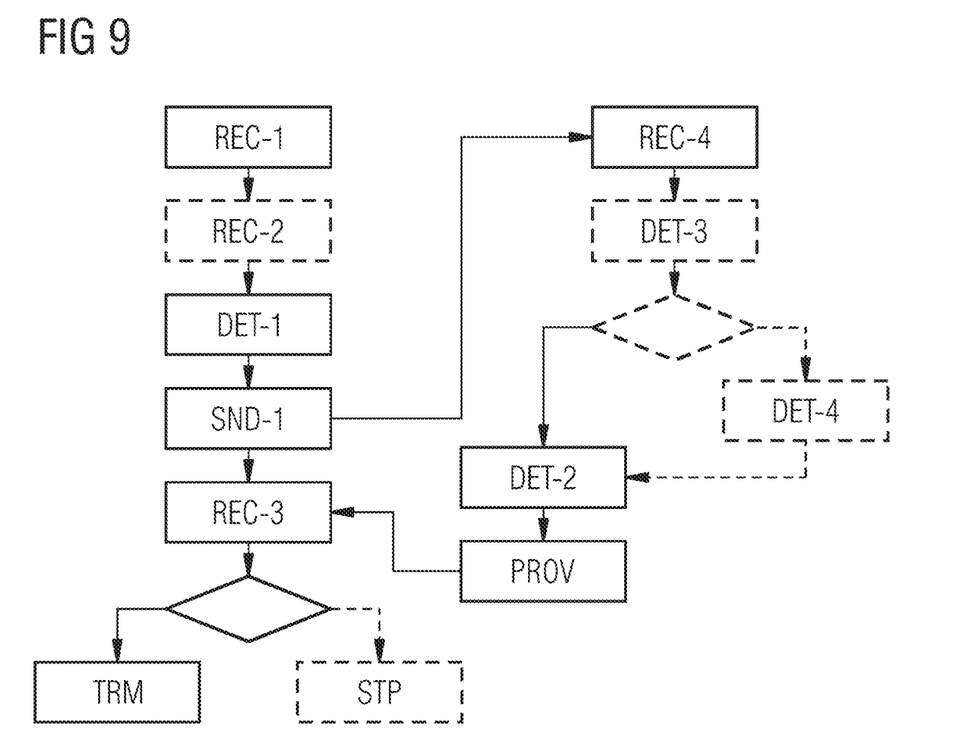
FIG. 9 shows a third example embodiment of the method for the transmission of a data set.

FIG. 9 shows a third example embodiment of a method for the transmission of a data set 50. The third example embodiment corresponds to an interaction between the second example embodiment of the method for the transmission of a data set 50 and the second example embodiment of the method for providing data transmission information 80. This corresponds to an interaction between the data source 10 and the server 20. The steps of the third example embodiment can comprise all the advantageous embodiments and developments of the corresponding steps of the second example embodiment of the method for the transmission of a data set 50 and the second example embodiment of the method for providing data transmission information 80.

Where not explicitly stated, but advisable and within the spirit of the invention, individual example embodiments, individual sub-aspects or features thereof can be combined or interchanged without departing from the scope of the present invention. Where applicable, advantages of the invention described with reference to one example embodiment also apply to other example embodiments without being explicitly named.

The invention claimed is:

1. A computer-implemented method for transmission of a data set to a central data store, the method comprising:
   receiving, by a data source, the data set;
   determining, by the data source, a data classification based on the data set;
   receiving, by the data source, country information;
   sending, by the data source, the data classification and the country information to a server;
   receiving, by the data source, data transmission information from the server, the data transmission information being based on the data classification and the country information, and the data transmission information relating to permissibility of the transmission of the data set; and
   transmitting, by the data source, the data set to the central data store in dependence on the data transmission information.

2. The method of claim 1, wherein the sending the data classification sends the data classification by invoking an interface function of the server, and the data transmission information is an output value of the interface function.

3. The method of claim 1, wherein the country information includes source country information and target country information.

4. The method of claim 1, wherein the data transmission information includes a status variable, and the transmitting the data set transmits the data set upon the status variable assuming a first value and not a second value.

5. The method of claim 1, wherein the data classification is contained in metadata of the data set.

6. The method of claim 1, wherein the determining the data classification determines the data classification by applying at least one of a regular expression or a trained function to the data set.

7. A computer-implemented method for provision of data transmission information, the method comprising:
   receiving, by a server, a data classification and country information;
   determining, by the server, data transmission information based on the data classification and the country information; and
   providing, by the server, the data transmission information for a data source.

8. The method of claim 7, further comprising:
   determining a first classifier, the first classifier being stored in a first data table in relation to at least one of the country information or the data classification,
   wherein the determining the data transmission information determines the data transmission information based on the first classifier.

9. The method of claim 8, further comprising:
   determining a second classifier, the second classifier being stored in a second data table in relation to contract information,
   wherein the determining the data transmission information determines the data transmission information based on the second classifier.

10. The method of claim 9, wherein the determining the second classifier only determines the second classifier when the first classifier has a defined value.

11. The method of claim 7, further comprising:
    determining, by the server, a modified data classification by applying at least one of a regular expression or a trained function to the data classification.

12. The method of claim 1, wherein the data transmission information was provided via a computer-implemented method for provision of data transmission information, comprising:
    receiving, by the server, the data classification and the country information;
    determining, by the server, the data transmission information based on the data classification and the country information; and
    providing, by the server, the data transmission information for the data source.

13. A data source for transmitting a data set to a central data store, the data source comprising:
    an interface configured to
       receive the data set,
       receive country information,
       send a data classification and the country information to a server,
       receive data transmission information from the server, the data transmission information being based on the data classification and the country information, and the data transmission information relating to permissibility of transmission of the data set, and
       transmit the data set to the central data store in dependence on the data transmission information; and
    at least one processor configured to determine the data classification based on the data set.

14. A server for providing data transmission information, the server comprising:
    an interface configured to
       receive a data classification and country information, and
       provide the data transmission information for a data source; and
    at least one processor configured to determine the data transmission information based on the data classification and the country information.

15. A non-transitory computer program product storing a computer program, directly loadable into a first storage of a client, including program sections for carrying out the method of claim 1 when the program sections are executed by the client.

16. A non-transitory computer-readable storage medium storing program sections, readable and executable by a client, for carrying out the method of claim 1 when the program sections are executed by the client.

17. The method of claim 2, wherein the country information includes source country information and target country information.

18. The method of claim 2, wherein the data transmission information includes a status variable, and the transmitting of the data set transmits the data set upon the status variable assuming a first value and not a second value.

19. The method of claim 2, wherein the data classification is contained in metadata of the data set.

20. The method of claim 6, wherein the trained function is a trained neural network.

21. A non-transitory computer program product storing a computer program, directly loadable into a first storage of a server, including program sections for carrying out the method of claim 7 when the program sections are executed by the server.

22. A non-transitory computer-readable storage medium storing program sections, readable and executable by a server, for carrying out the method of claim 7 when the program sections are executed by the server.

23. The method of claim 1, wherein the data classification relates to a type of the data set or a type of content of the data set.

24. The method of claim 1, wherein the data classification includes an indication of whether the data set contains personal data.

25. The method of claim 1, wherein the determining determines the data classification based on:
   a file name, file extension or format of the data set; or
   a type or serial number of an apparatus that generated the data set.

26. The method of claim 1, wherein the data classification comprises an indication that the data set contains one of non-confidential data, anonymized data or confidential data.

27. The method of claim 1, wherein the data classification comprises a first key-value pair and a second key-value pair, the first key-value pair including a first key of medical data and a first value, the first value being true or false based on whether the data set includes medical data, the second key-value pair including a second key of personal data and a second value, and the second value being true or false based on whether the data set includes personal data.

28. The method of claim 1, wherein the country information includes a source country in which the data source is located.

29. The method of claim 28, wherein
   the method further comprises
      receiving, by the data source, a first address of the central data store, the first address including a URL or an IP address, and
      determining, by the data source, a target country in which the central data store is located based on the first address;
   the sending sends the target country to the server; and
   the data transmission information is based on the data classification and the target country.

30. The method of claim 7, further comprising:
   determining a source country in which the data source is located based on an IP address of the data source or a serial number of the data source, and
   wherein the determining data transmission information determines the data transmission information based on the data classification and the source country.

* * * * *